(12) United States Patent  (10) Patent No.: US 8,777,999 B2
Songer  (45) Date of Patent: Jul. 15, 2014

(54) VARIABLE ANGLE LOCKING PLATE SYSTEM

(76) Inventor: Matthew N. Songer, Marquette, MI (US)

( * ) Notice: Subject to any disclaimer, the term of this patent is extended or adjusted under 35 U.S.C. 154(b) by 130 days.

(21) Appl. No.: 13/179,117

(22) Filed: Jul. 8, 2011

(65) Prior Publication Data

US 2012/0010666 A1    Jan. 12, 2012

Related U.S. Application Data

(60) Provisional application No. 61/362,611, filed on Jul. 8, 2010.

(51) Int. Cl.
*A61B 17/80* (2006.01)

(52) U.S. Cl.
USPC .......................... 606/290; 606/293

(58) Field of Classification Search
USPC ...................... 606/70–71, 280–299
See application file for complete search history.

(56) References Cited

U.S. PATENT DOCUMENTS

| | | | |
|---|---|---|---|
| 4,388,921 A | 6/1983 | Sutter et al. | |
| 5,180,381 A | 1/1993 | Aust et al. | |
| 5,429,639 A | 7/1995 | Judet | |
| 5,954,722 A | 9/1999 | Bono | |
| 6,235,033 B1 | 5/2001 | Brace et al. | |
| 6,331,179 B1 | 12/2001 | Freid et al. | |
| 6,602,255 B1 | 8/2003 | Campbell et al. | |
| 6,679,883 B2 | 1/2004 | Hawkes et al. | |
| 6,955,677 B2 | 10/2005 | Dahners | |
| 7,112,222 B2 | 9/2006 | Fraser et al. | |
| 7,678,116 B2 | 3/2010 | Truckai et al. | |
| 7,682,375 B2 | 3/2010 | Ritland | |
| 7,682,379 B2 | 3/2010 | Mathieu et al. | |
| 7,708,765 B2 | 5/2010 | Carl et al. | |
| 7,722,649 B2 | 5/2010 | Biedermann et al. | |
| 2004/0210223 A1* | 10/2004 | Pisharodi | 606/71 |
| 2005/0154392 A1* | 7/2005 | Medoff et al. | 606/69 |
| 2006/0235399 A1* | 10/2006 | Carls et al. | 606/69 |
| 2008/0119895 A1 | 5/2008 | Manceau | |
| 2008/0234677 A1 | 9/2008 | Dahners et al. | |
| 2008/0234752 A1 | 9/2008 | Dahners | |
| 2008/0306550 A1* | 12/2008 | Matityahu | 606/290 |
| 2009/0048605 A1 | 2/2009 | Yurek | |
| 2009/0157121 A1* | 6/2009 | Harris et al. | 606/280 |
| 2009/0318978 A1* | 12/2009 | Podgorski et al. | 606/290 |
| 2012/0053638 A1* | 3/2012 | Rusch | 606/287 |

* cited by examiner

*Primary Examiner* — Matthew Lawson
(74) *Attorney, Agent, or Firm* — Wood, Phillips, Katz, Clark & Mortimer (57) ABSTRACT

A plate system for controlling relative positions of adjacent bone portions. The plate system has a plate with first and second spaced through bores, an insert consisting of first and second insert pieces in the first bore, and a first fastener. The first plate bore, first and second insert pieces, and first fastener are configured so that advancing of the first fastener into the first bore and one of the adjacent bone portions causes the first fastener to be fixed in a selected one of a plurality of different potential angular orientations for the first fastener. The system further has a second fastener for direction through the second bore and into the other of the adjacent bone portions.

24 Claims, 6 Drawing Sheets

VARIABLE ANGLE LOCKING PLATE SYSTEM

CROSS-REFERENCE TO RELATED APPLICATIONS

This application is a non-provisional of U.S. Ser. No. 61/362,611 filed Jul. 8, 2010.

BACKGROUND OF THE INVENTION

1. Field of the Invention

This invention relates to systems for fixing together, or controlling the relative positions of, adjacent bone portions.

2. Background Art

A multitude of systems currently exists for purposes of fixing together, or otherwise controlling the relative positions of, adjacent bone portions. As an example, a bone fracture may be prepared for healing by utilizing a plate that strategically accepts screws so that the bone portions, between which the fracture site is located, are held positively together, potentially with a compressive force.

Bone portions/discs are commonly required to be fixed or stabilized in the cervical spine. This may be accomplished so that the adjacent disks are either fixed in relationship to each other or interconnected so that controlled movement therebetween is permitted.

In designing such systems, the main objective is to reliably and positively interconnect adjacent bone portions for their intended cooperation, be it static or dynamic in nature. It is also an objective to design versatile systems that will be flexible in terms of how they attach to adapt to different bone sites and conditions. It is further an objective in this field to design systems that can be conveniently attached, yet will not be prone to loosening over their intended life.

SUMMARY OF THE INVENTION

In one form, the invention is directed to a plate system for controlling relative positions of adjacent bone portions. The plate system has a plate with first and second spaced through bores, an insert consisting of first and second insert pieces in the first bore, and a first fastener. The first plate bore, first and second insert pieces, and first fastener are configured so that the first fastener extended through the first bore into one of the adjacent bone portions causes the first fastener to be fixed in a selected one of a plurality of different potential angular orientations for the first fastener. The system further has a second fastener for direction through the second bore and into the other of the adjacent bone portions.

In one form, at least one of the insert pieces is made thin enough to deform under a force produced by the first fastener as the first fastener is advanced through the first bore.

In one form, the first and second insert pieces each has a concave surface and the first fastener has a rounded head and a shank. The rounded head has a convex surface that cooperates with the concave surfaces.

In one form, the convex surface has threads, the concave surfaces have threads, and the threads on the convex surface and concave surfaces cooperate as the first fastener is advanced through the first bore in different angular orientations.

In one form, the plate system has a second insert including third and fourth insert pieces in the second bore through which the second fastener is advanced.

In one form, the first bore has a central axis and a peripheral wall that is concave opening towards the central axis. At least one of the insert pieces has a convex external surface that is complementary in shape to the peripheral wall so that the at least one insert piece can be guided in movement relative to the peripheral wall, thereby to change an angular orientation of the first fastener within the first bore.

In one form, the first and second insert piece have components that interdigitate.

In one form, the shank on the first fastener has threads with a different pitch than a pitch for the threads on the convex surface of the rounded head on the first fastener.

In one form, the first bore has a first axis. With the second fastener directed through the second bore and into the other of the adjacent bone portions, advancing of the first fastener through the first bore causes one of the first and second insert pieces to wedge the plate in a direction transversely to the first axis to cause the bone portions to be urged towards each other.

In one form, there is a location tab on one of the insert pieces and plate and a slot on the other of the one insert piece and plate. The location tab and slot cooperate to maintain a selected orientation of the one insert piece and plate.

In one form, the first and second bores are spaced along a first line and with the first and second fasteners directed into their respective bone portions, one of the fasteners is allowed to shift within its respective bore along the first line.

In one form, the bore through which the one of the fasteners extends is elongate along the first line.

In one form, the bore through which the one of the fasteners extends is the first bore.

In one form, the first and second insert pieces each has guide structure that cooperates with guide structure on the plate to guide movement between the first and second insert pieces and plate.

In one form, the first and second bores are spaced along a first line and the guide structure guides relative movement between the first and second insert pieces and plate in translation along the first line.

In one form, the plate system further includes a second insert and there are components cooperating between one of the inserts and plate to allow the one of the inserts to be controllably set at different positions within its respective bore.

In one form, the cooperating components are ratchet components.

In one form, the one of the fasteners is directed through an insert within the elongate bore. The insert within the elongate bore and plate have angled surfaces that cooperate to at least one of: a) limit movement of the insert within the elongate bore; and b) guide movement of the insert within the elongate bore.

In one form, there is a second insert in the second bore through which the second fastener extends and there are aligned bores in one of the fasteners and plate to accept a locking pin.

In one form, the plate system further includes an insert within the second bore through which the second fastener extends. The first and second bores are spaced along a first line. One of the bores is elongate to allow movement therein of its respective insert along the first line. The other of the bores cooperates with its respective insert so that the insert within the other of the bores is not movable within the other of the bores along the first line.

DETAILED DESCRIPTION OF THE PREFERRED EMBODIMENT

Figure 1:
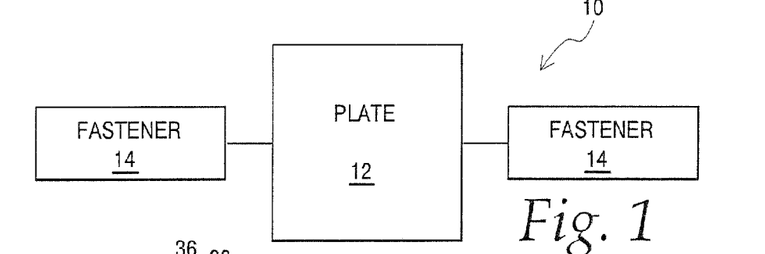
FIG. 1 is a schematic representation of a plate system for controlling relative positions of adjacent bone portions, according to the present invention.

In FIG. 1, a basic system contemplated by the invention is shown at 10 and consists of a plate 12 with which separate fasteners 14 are associated. The fasteners 14 are typically threaded and directed into the adjacent bone portions and cooperate with the plate 12 to effect the desired fixation/stabilization between the bone portions. Commonly, the fasteners 14 will be directed into the plate 12 at spaced locations and potentially at different angles to achieve this end.

One problem that has been contended with is maintaining the plate 12 positively against the adjacent bone portions.

Figure 2:
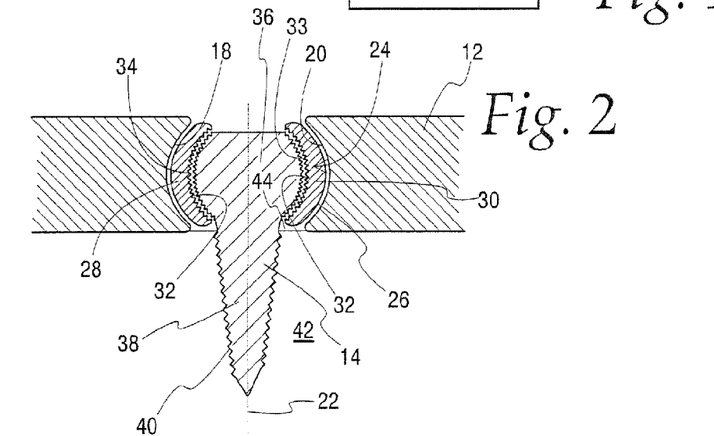
FIG. 2 is a partial cross-sectional view of a fastener directed through a bore in a plate on an exemplary system, as shown in FIG. 1, and threadably engaged with insert pieces within the plate bore.

In one form, as shown in FIG. 2, the plate 12 has a through-bore 18 bounded by a peripheral wall 20 that is concave opening towards a central axis 22. An insert 24 has a convex external surface 26 that nominally matches/is complementary to the shape of the peripheral wall 20. The insert 24 may be made with one or multiple pieces. In this embodiment, the insert 24 is made from separate pieces 28, 30. The insert pieces 28, 30 may be identical to each other, though this is not required.

The insert pieces 28, 30 each has internal threads 32 on a concave surface 33 defined cooperatively by the insert pieces and opening toward the axis 22. The threads 32 cooperate with threads 34 on an external surface of the fastener 14. The fastener 14 has an enlarged, round head 36 with a convex outer surface on which the threads 34 are formed, and a shank 38 with threads 40. The convex outer surface cooperates with the concave surface 33.

The threads 32, 34 cooperate to allow the fastener 14 to be directed into a bone portion 42 at different angles. The rounded configuration of the head 36 causes the head 36 to progressively wedge the insert pieces 28, 30 away from each other to be positively locked within the bore 18 against the wall 20 as the fastener is advanced into the bore 18.

With the fastener 14 fully inserted, the threads 32, 34 cooperate in a manner that the fastener 14 is not prone to turning in a loosening direction or otherwise loosening once it is fully torqued. This locking/anti-backout mechanism is effected with the fastener 14 directed into the bone portion 42 at virtually any required angular orientation.

To assure that the plate 12 is borne positively against the surface 44 of the bone portion 42, the fastener 14 is made with different thread configurations on the head 36 and shank 38. More specifically, the threads 40 on the shank 38 have a greater pitch than that of the threads 34 on the head 36. Consequently, as the fastener 14 is turned, it moves incrementally at a greater rate along the axis 22 into the bone portion 42 than the head 36 moves relative to the plate 12. As a result, the plate 12 is drawn positively against the bone surface 44, initially eliminating any potential gap and thereafter creating a compressive connection.

In one form, the insert pieces 28, 30 are made thin enough to deform under the force of the advanced fastener 14. The curvatures of the peripheral wall 20 and external surface 26 may be mismatched so that as this compression occurs, the pieces 28, 30 firmly lock in place. As but one example, the curvatures may be made of different size and/or shape to allow this compressive locking resulting from the forced deformation of the insert pieces 28, 30 within the bore 18.

Figures 3, 4:
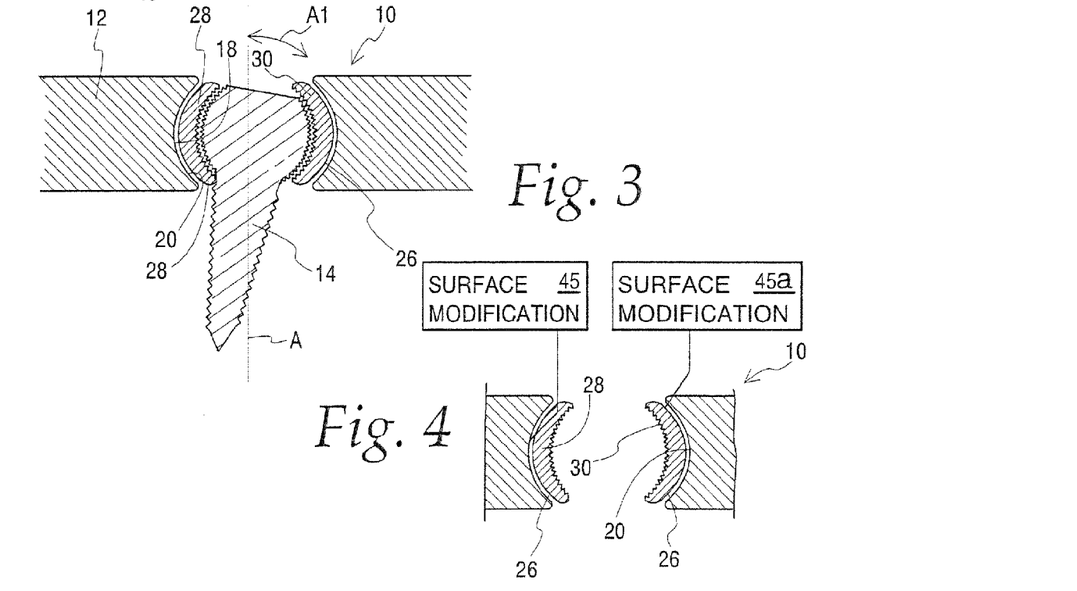
FIG. 3 is a view as in FIG. 2 wherein the fastener has a different orientation.
FIG. 4 is a view as in FIG. 2 without the fastener in place and showing surface modifications to enhance connection between the insert pieces and plate.
Figure 5:
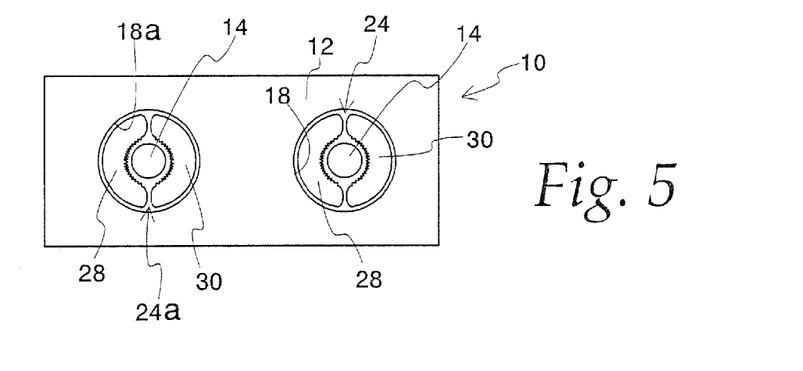
FIG. 5 is a plan view of one specific form of system as in FIG. 1 for a static application.

In FIGS. 3-5, different views of the system 10 are shown. In FIG. 3, the fastener 14 is shown at a different angle than in FIG. 2. The insert pieces 28, 30 and peripheral wall 20 on the plate 12 are configured so that the inserts 28, 30 can be guidingly repositioned relative to the plate 12 before tightening of the fastener 14. This guided movement may be around the axis A of the bore 18. A slight guided shifting of the inserts 28, 30 may be permitted within the bore 18 as indicated by the double-headed arrow A1.

To facilitate more positive locking, the bore wall 20 may be roughened or otherwise modified from a smooth shape. For example, the surface of the bore wall 20 may be modified by incorporating some irregularity such as projections, depressions, irregular contours, etc. The cooperating surfaces 26 on the insert pieces 28, 30 may be similarly treated so that there is more positive engagement between the insert pieces 28, 30 and plate 12 as the fastener 14 is tightened. These surface modifications are shown schematically for the bore wall 20 and surfaces 26 of the insert pieces 28, 30 in FIG. 4 at 45, 45a. The surface modification may be made for all embodiments herein, including but not limited to, that shown in FIGS. 7 and 8.

In FIG. 5, the plate 12 and insert pieces 28, 30 are shown in a static application. A bore 18a is shown spaced from the bore 18. With a fastener 14 directed through the pieces 28, 30 in each of the inserts 24, 24a, the insert pieces 28, 30 fixedly lock in their respective bore 18, 18a.

Figure 6:
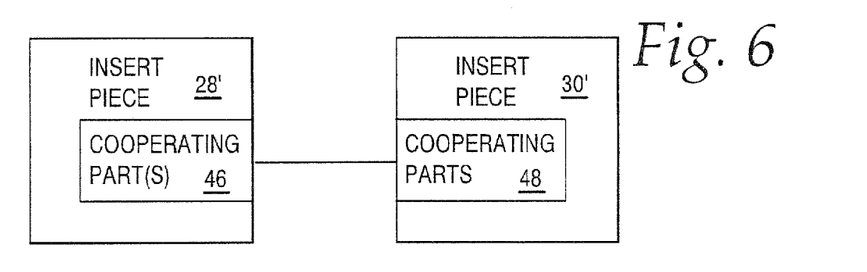
FIG. 6 is a schematic representation of cooperating parts on insert pieces to control relative movement therebetween.

The insert pieces 28, 30 may be separate components that simply abut, or are in close proximity within their respective bore. Alternatively, as shown in FIG. 6, insert pieces 28', 30' may have one or more cooperating parts 46, 48 that interact to control relative movement between the pieces 28', 30' in one or more planes. As an example, the cooperating parts 46, 48 may be components that interdigitate.

Figures 7, 8:
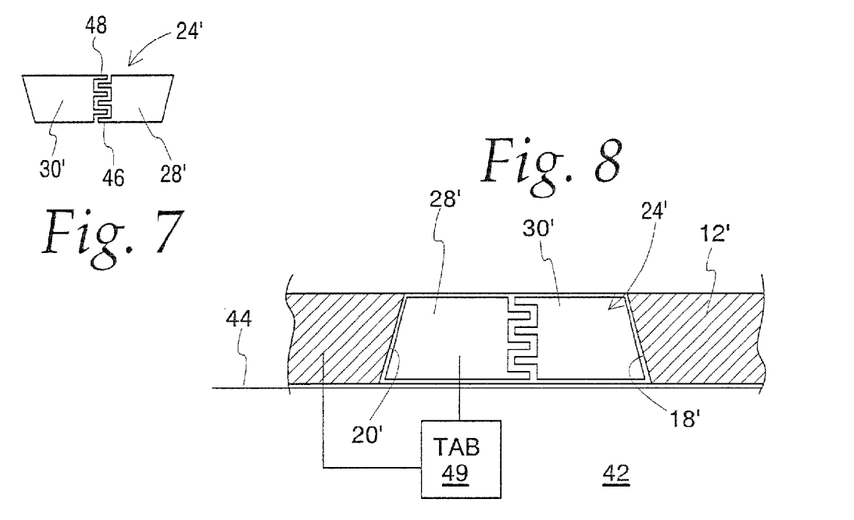
FIG. 7 is an elevation view of insert pieces with exemplary cooperating parts, as shown schematically in FIG. 6.
FIG. 8 is a partial cross-sectional view of a plate with the insert pieces of FIG. 7 in place.

One example of the interdigitating insert pieces 28', 30' is shown for the insert 24' in FIG. 7, wherein the parts 46, 48 are intermeshing teeth. In FIG. 7, the insert pieces 24', 26' have a tapered shape which requires a complementary shape on a bore 18' on a plate 12', as shown in FIG. 8. This configuration avoids separation of the insert from the plate 12' since it becomes captured by the complementary tapered wall 20' against the bone portion surface 44.

A tab 49 may be provided on one or both of the insert pieces 28', 30' to cooperate with the plate 12' to control axial migration of the insert pieces 28', 30' towards the bone portion 42.

Further, this interdigitation feature can be incorporated into any of the embodiments described herein or otherwise contemplated within the inventive scope.

Figure 9A:
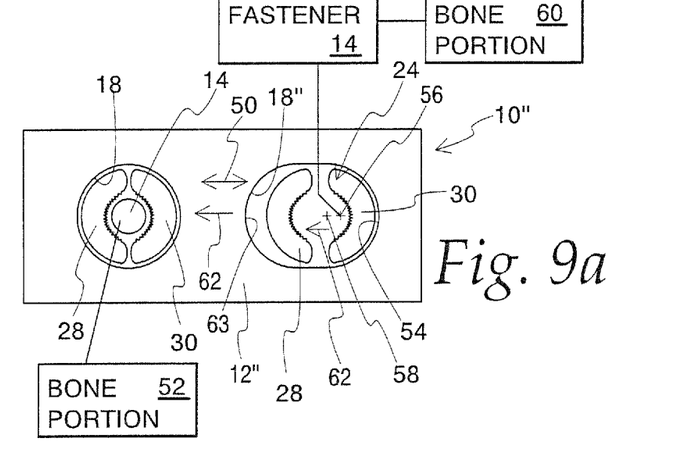
FIG. 9 is a view as in FIG. 5 of a modified form of system wherein one of the fasteners is in a fixed position, relative to a bone portion and the plate, and a separate fastener is used to shift an adjacent bone portion towards the bone portion with the fixed fastener, as shown sequentially in FIGS. 9a and 9b.
Figure 9B:
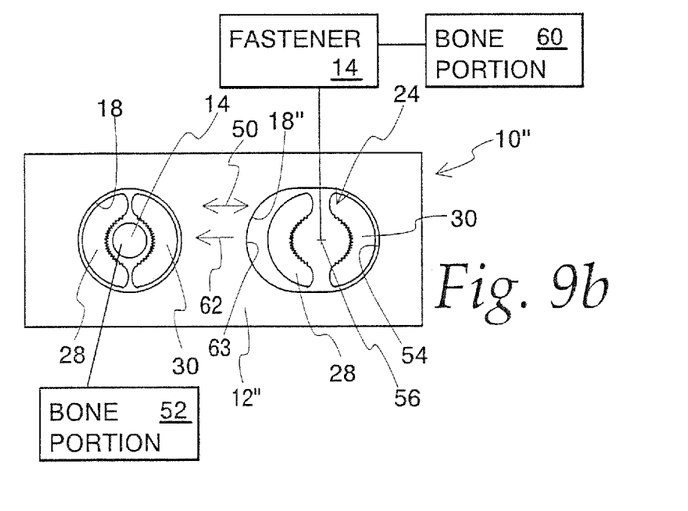

In FIG. 9, a system is shown at 10" with a plate 12" having a bore 18, the same as the bores 18, 18a in FIG. 4, and a modified bore 18" that is elongate in a lengthwise direction of the plate 12", as indicated by the double-headed arrow 50. The insert pieces 28, 30 are fixed in the bore 18 through a fastener 14 to a bone portion 52 as described above.

The insert pieces 28, 30 for the insert 24 in the bore 18" are installed at the lengthwise end 54 of the bore 18" furthest from the bore 18. In this position, an insertion location 56 for the fastener 14, which is pre-drilled, is shifted from the central axis 58 for the insert pieces 28, 30 slightly towards the bore end 54. As the fastener 14 is tightened, the fastener 14 wedges progressively against the insert piece 30 that is abutted to the bore end 54, and thereby produces a force on a bone portion 60, adjacent the bone portion 52, tending to urge the same in the direction of the arrow 62 towards the other bone portion 52, thereby reducing the spacing, or generating a compressive force, therebetween. The elongate configuration of the bore 18" allows the insert piece 30 to shift with the bone portion 60 relative to the plate 12" in the direction of the arrow 62.

The spacing between the insert piece 28 and end 62 of the bore 18'", remote from the bore end 54, is shown substantially greater than it would practically be to facilitate description of the operation. Only a slight shifting of the bone portion 60 is contemplated and thus the lengthwise spacing between the insert piece 28 and the bore end 63 could be reduced to the point that the insert pieces will be maintained in relatively close proximity between the bore ends 54, 63. Alternatively, a larger space can be maintained by interconnecting the insert pieces, as in FIG. 6, or maintaining the insert pieces and plate together preparatory to fastener tightening by structure described hereinbelow.

In each case, the insert pieces 28, 30 are movable relative to each other in a direction transverse to an axis of the fastener 14 extending into the bore 18" and between the insert pieces 28, 30. The insert pieces 28, 30 extend only partially around the axis of the fastener 14 as it is extended into the bore 18" in a direction along the fastener axis.

Figure 10:
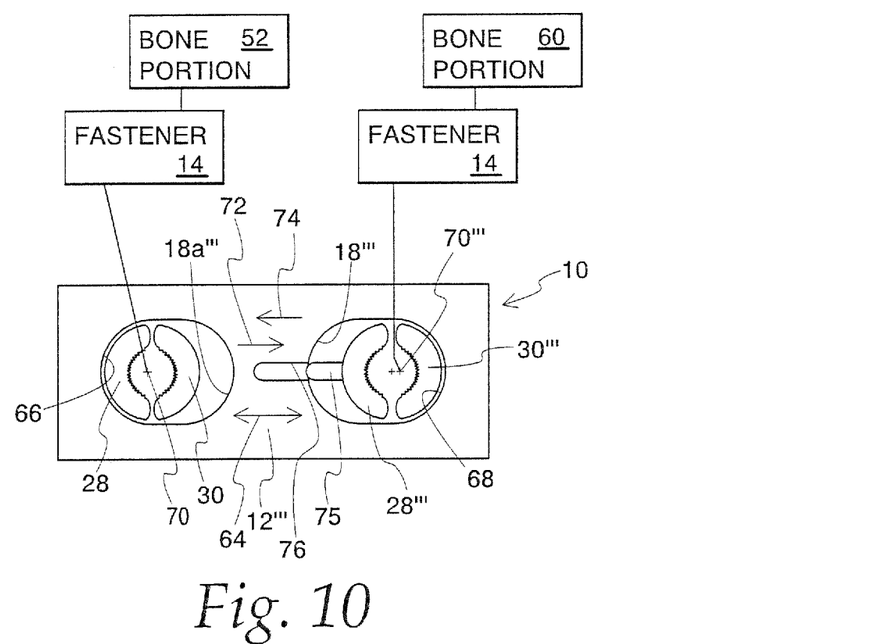
FIG. 10 is a view as in FIG. 9 of a modified form of system wherein separate fasteners in adjacent bone portions can each be shifted towards each other and relative to a plate.

In FIG. 10, a modified form of plate is shown at 12'" with an elongate bore 18'", configured as the bore 18" in FIG. 9, and a similarly configured bore 18a'". Each of the bores 18'", 18a'" is elongate in the direction of the length of the plate 12'", as indicated by the double-headed arrow 64.

The bore 18a'" has a lengthwise end 66, furthest from the bore 18'", to which the insert piece 28 abuts. The lengthwise end 68 of the bore 18'", furthest from the bore 18a'", abuts to an insert piece 30'". The insert pieces 28, 30 cooperate as previously described for the insert pieces 28, 30 in the bore 18" in FIG. 9, with the insert piece 30'" cooperating with an insert piece 28'" in like fashion in the bore 18'".

The insertion location 70 for the fastener 14 in the bore 18a'" is offset from the lengthwise center of the insert pieces 28, 30 towards the bore end 66, with the corresponding insert location 70'" for the fastener 14 in the bore 18'" offset from lengthwise center towards the bore end 68.

The fasteners 14 directed through the inserts 28, 30 and 28'", 30'" cooperate as the fastener 14 does with the insert pieces 28, 30 in the bore 18" in FIG. 9. That is, the fastener 14, directed through the insert pieces 28, 30 into the bone portion 52, bears against the insert piece 28 and wedges so as to progressively shift the bone portion 52 in the direction of the arrow 72, with the inserted fastener 14 in the bore 18'" shifting the bone portion 60 oppositely in the direction of the arrow 74.

The insert piece 28'" is slightly modified by reason of having a location tab 75 that is guided in a slot 76 on the plate 12'". This maintains the preferred/selected orientation of the insert piece 28'" preparatory to installing the fastener 14 that effects shifting thereof. A similar arrangement may be provided for the insert pieces 28, 30 in the bore 18a'".

Figure 11:
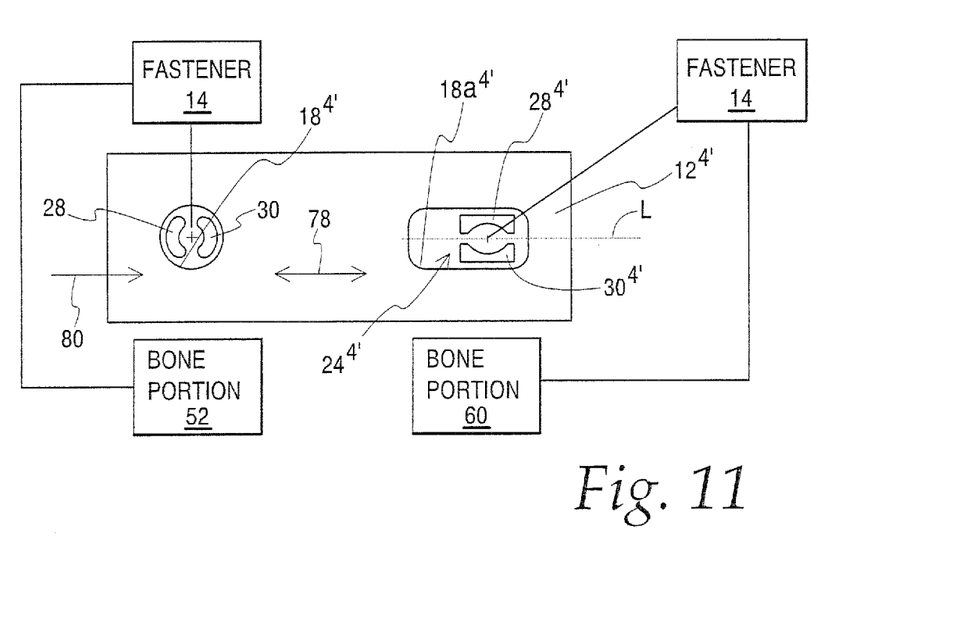
FIG. 11 is a view as in FIGS. 9 and 10 of a further modified form of system that is dynamic so as to permit controlled movement of the adjacent bone portions relative to each other.

The invention also contemplates that there can be dynamic compression between the bone portions 52, 60, as shown in FIG. 11. In this embodiment, a further modified form of plate is shown at $12^{4'}$ with a bore $18^{4'}$, in which insert pieces 28, 30 are fixed, and a spaced bore $18a^{4'}$, that is elongate in a lengthwise direction of the plate $12^{4'}$, as indicated by the double-headed arrow 78.

In this embodiment, insert pieces $28^{4'}$, $30^{4'}$ are placed into the bore $18a^{4'}$ with an interface line L therebetween parallel to the length of the plate $12^{4'}$. With a fastener 14 secured in the bone portion 60, and a fastener 14 secured in the bone portion 52, the insert pieces $28^{4'}$, $30^{4'}$ are allowed to shift within the bore $18a^{4'}$ lengthwise therewithin in a guided manner. This permits a modicum of shifting of the bone portions 52, 60, as when a lengthwise load is applied to the bone portion 52 in the direction of the arrow 80 that is generally parallel to a line between locations at which the first and second fasteners are directed into their respective bone portions.

Figure 12:
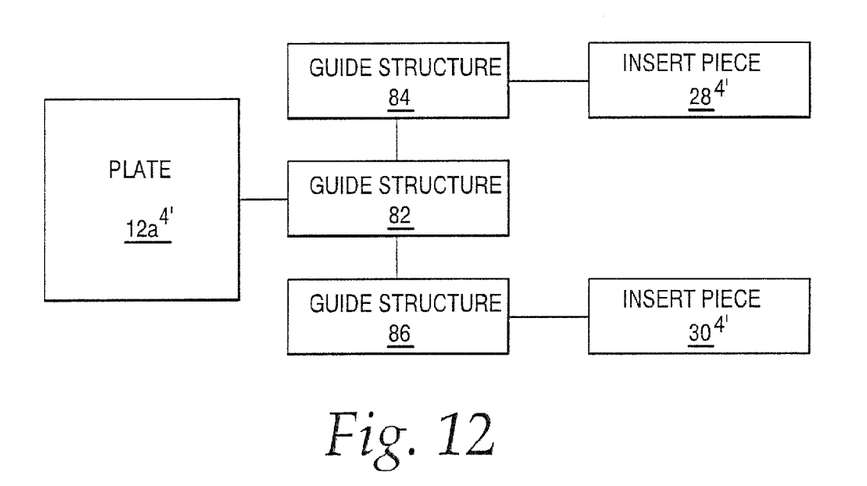
FIG. 12 is a schematic representation of guide structure cooperating between movable insert pieces and a plate for a dynamic system as in FIG. 11.

Preferably, the plate $12^{4'}$ guides lengthwise translating movement of the insert pieces $28^{4'}$, $30^{4'}$ relative thereto. Exemplary structure is shown schematically in FIG. 12 for the plate $12^{4'}$, through which the guided movement may be effected. More specifically, the plate $12^{4'}$ has guide structure at 82 that cooperates with guide structure 84, 86, respectively on the insert pieces $28^{4'}$, $30^{4'}$. The cooperating structure may be in the form of rails, pins and slots, etc. One skilled in the art could devise virtually an unlimited number of different guide structures to perform this function.

Figure 13:
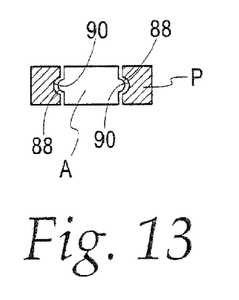
FIGS. 13-15 are partial cross-sectional views showing connections between cooperating insert pieces and a wall surrounding an elongate plate bore within which the insert pieces reside, as in the systems in FIGS. 11 and 12.
Figure 14:
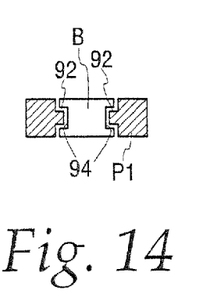
Figure 15:
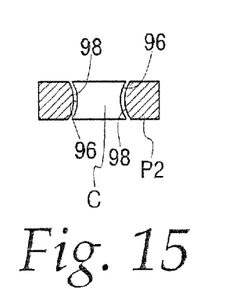

In FIGS. 13-15, three optional guide structures are shown for insert pieces identified as A, B and C, successively therein, and corresponding generally to the insert $24^{4'}$ in FIG. 11 made up of the insert pieces $28^{4'}$, $30^{4'}$.

The insert A in FIG. 13 has oppositely projecting ribs, or other discrete component(s) 88, cooperating one each in complementary slots 90 on the plate P, corresponding to the plate $12^{4'}$.

In FIG. 14, the plate P1 has inwardly projecting components 92 that move one each in complementary slots 94 on the insert B.

In FIG. 15, the insert C has oppositely facing concave surfaces 96 cooperating with complementary convex surfaces 98 on the plate P2.

Figure 16:
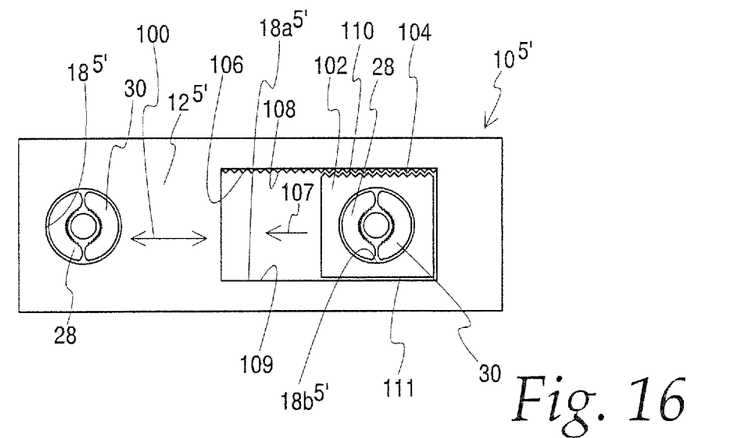
FIG. 16 is a view as in FIG. 11 of a further modified form of dynamic system.

In FIG. 16, a further modified form of system is shown at 10⁵' with a plate 12⁵' having a length indicated by the double-headed arrow 100. A fixed bore 18⁵' is provided for insert pieces 28, 30 as hereinabove described.

A separate bore 18a⁵' is provided and is elongate parallel to the length of the plate 12⁵'. A second insert 102 is provided with a bore 18b⁵' for insert pieces 28, 30. The insert pieces 28, 30 can potentially be pivoted guidingly within the bore 18b⁵' around multiple axes.

The insert 102 is guided in a lengthwise direction within the bore 18a⁵' through any appropriate arrangement, including but not limited to those discussed above with respect to FIGS. 13-15.

In one exemplary embodiment, there are components, independent of the fasteners, on the insert 102 and plate 12⁵' that allow the insert to be controllably set at different lengthwise positions within the bore 12⁵'. While not limiting, as one example, there are conventional-type ratchet components 104, 106, shown somewhat schematically respectively on the insert 102 and the plate 12⁵', that cooperate to allow one-directional lengthwise shifting of the insert 102 within the bore 18a⁵' towards the fixed bore 18⁵', as indicated by the arrow 107. Ratchet and/or guide teeth may be provided at one or more of the lengthwise edges 108, 109 bounding the bore 18a⁵' and extending in a parallel direction to cooperate with teeth on edges 110, 111, respectively, on the insert 102.

An appropriate tool (not shown) may be utilized to controllably reposition/drive the insert 102 to the desired location, thereby to establish the desired relationship between the bone portions 52, 60 associated with the respective inserts. Through this arrangement, uniplanar/unidirectional dynamic compression between the bone portions 52, 60 can be developed.

Figure 17:
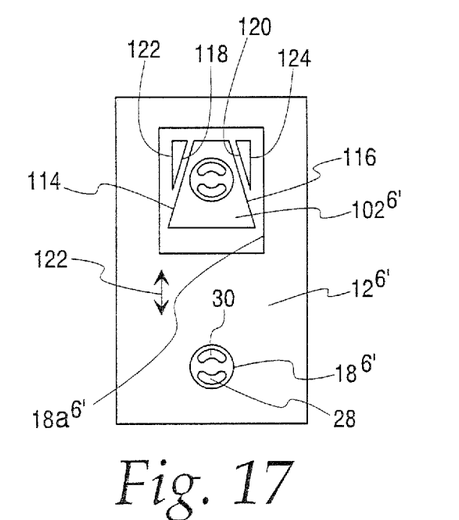
FIG. 17 is a view as in FIGS. 11 and 16 of a still further modified form of dynamic system.

In an alternative form, as shown in FIG. 17, an insert 102⁶', corresponding to the insert 102, is provided on a plate 12⁶' with a fixed bore 18⁶' and an elongate bore 18a⁶' corresponding to the bore 18a⁵' in FIG. 16 and with insert pieces 28, 30 therein. The plate 12⁶' is shown with its lengthwise extent, indicated by the double-headed arrow 122, aligned vertically so that the insert 102⁶' tends to shift downwardly under the force of gravity. The insert 102⁶' has angled cam/guide surfaces 114, 116 that cooperate respectively with facing, and similarly angled, surfaces 118, 120, on components 122, 124, respectively. The surfaces 114, 116 converge in an upward direction whereby upward shifting of the insert 102⁶' is arrested by the components 122, 124 as the insert 102⁶' becomes locked through a wedging action, thereby to limit upward vertical movement. Accordingly, relative movement of the bone portions 52, 60 associated with the separate inserts is permitted but confined in a vertical direction.

The surfaces 114, 116; 118, 120 preferably have cooperating structure that guides relative lengthwise movement therebetween. The structures described above that guide components, as in FIGS. 13-15, may be utilized. Others may be devised as appropriate.

Figure 18:
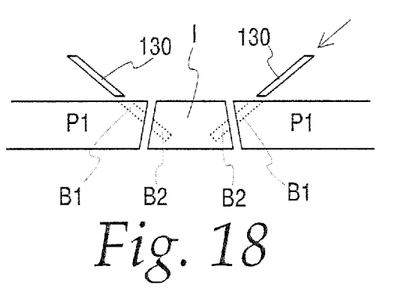
FIG. 18 is a partial cross-sectional view as in FIG. 8 wherein optional locking pins are provided for cooperating insert pieces.

As shown in FIG. 18, it also may be desirable to fix an insert, as shown schematically at I relative to a plate identified as P1 in this Figure. One or more locking pins 130 may be directed through pre-drilled aligned bore parts B1, B2, respectively through the plate P1 and insert I.

It should be understood that the invention contemplates that the inserts may be made of one piece or more than three pieces. A two piece construction is desired for the versatility it affords while at the same time facilitating assembly.

Many variations of the structure described above are contemplated without departing from the invention. Some, but not all, of the contemplated variations are described below.

While the cooperating surfaces on the inserts 28, 30 and plate 12 are shown to be respectively convex and concave, this curvature could be reversed so that the inserts 28, 30 have a convex shape cooperating with a complementary surface configuration on the plate 12.

These surfaces could take virtually any other shape that permits the aforementioned controlled interlocking of the inserts and plate.

While the cooperating threaded surfaces on the fastener 14 and inserts 28, 30 are also shown to be of complementary concave and convex shapes, these surfaces might have any shape that permits the progressive wedging action as the fastener 17 is advanced. As one example, the fastener may have a conical shape to cooperate with inserts having surfaces with a constant diameter. Alternatively, the insert surfaces might be of another shape that has a non-constant diameter.

The foregoing disclosure of specific embodiments is intended to be illustrative of the broad concepts comprehended by the invention.

The invention claimed is:

1. A plate system for controlling relative positions of adjacent bone portions, the plate system comprising:
a plate having first and second spaced through bores;
an insert comprising first and second insert pieces in the first bore,
the first and second insert pieces movable in their entirety each relative to the other;
a first fastener,
the first plate bore, first and second insert pieces, and first fastener configured so that the first fastener extended through the first bore into one of the adjacent bone portions causes the first fastener to be fixed in a selected one of a plurality of different potential angular orientations for the first fastener; and
a second fastener for direction through the second bore and into the other of the adjacent bone portions.

2. The plate system according to claim 1 wherein at least one of the insert pieces is made thin enough to deform under a force produced by the first fastener as the first fastener is advanced through the first bore.

3. The plate system according to claim 1 wherein the first and second insert pieces each has a concave surface and the first fastener has a rounded head and a shank, the rounded head having a convex surface that cooperates with the concave surfaces.

4. The plate system according to claim 3 wherein the convex surface has threads, the concave surfaces have threads, and the threads on the convex surface and concave surfaces cooperate as the first fastener is advanced through the first bore in different angular orientations.

5. The plate system according to claim 3 wherein the first bore has a central axis and a peripheral wall that is concave opening towards the central axis and at least one of the insert pieces has a convex external surface that is complementary in shape to the peripheral wall so that the at least one insert piece can be guided in movement relative to the peripheral wall thereby to change an angular orientation of the first fastener within the first bore.

6. The plate system according to claim 4 wherein the shank on the first fastener has threads with a different pitch than a pitch for the threads on the convex surface of the rounded head on the first fastener.

7. The plate system according to claim 1 wherein the plate system comprises a second insert comprising third and fourth insert pieces in the second bore through which the second fastener is advanced.

8. The plate system according to claim 7 wherein the second fastener has a second axis and is directed through the second bore into the other of the adjacent bone portions in a direction along the second axis, and each of the third and fourth insert pieces extends only partially around the second axis with the second fastener extended through the second bore and between a part of each of the third and fourth insert pieces.

9. The plate system according to claim 1 wherein the first and second insert piece have components that interdigitate.

10. The plate system according to claim 1 wherein the first bore has a first axis, with the second fastener directed through the second bore and into the other of the adjacent bone portions, advancing of the first fastener through the first bore causes one of the first and second insert pieces to wedge the plate in a direction transversely to the first axis to cause the bone portions to be urged towards each other.

11. The plate system according to claim 1 wherein there is a location tab on one of the insert pieces or plate and a slot on the other of the one insert piece and plate, the location tab and slot cooperating to maintain a selected orientation of the one insert piece and plate.

12. The plate system according to claim 1 wherein the first and second bores are spaced along a first line and with the first and second fasteners directed into their respective bone portions, one of the fasteners is allowed to shift within its respective bore along the first line.

13. The plate system according to claim 12 wherein the bore through which the one of the fasteners extends is elongate along the first line.

14. The plate system according to claim 13 wherein the bore through which the one of the fasteners extends is the first bore.

15. The plate system according to claim 13, wherein the one of the fasteners is directed through the insert within the elongate bore and the insert within the elongate bore and plate have angled surfaces that cooperate to at least one of: a) limit movement of the insert within the elongate bore; b) guide movement of the insert within the elongate bore.

16. The plate system according to claim 1 wherein the first and second insert pieces each has guide structure that cooperates with guide structure on the plate to guide movement between the first and second insert pieces and plate.

17. The plate system according to claim 16 wherein the first and second bores are spaced along a first line and the guide structure guides relative movement between the first and second insert pieces and plate in translation along the first line.

18. The plate system according to claim 1 further comprising a second insert and there are components cooperating between one of the inserts and plate to allow the one of the inserts to be controllably set at different positions within its respective bore.

19. The plate system according to claim 18 wherein the cooperating components are ratchet components.

20. The plate system according to claim 1 wherein there is a second insert in the second bore through which the second fastener extends and there are aligned bores in one of the fasteners and plate to accept a locking pin.

21. The plate system according to claim 1 further comprising an insert within the second bore through which the second fastener extends, wherein the first and second bores are spaced along a first line, one of the bores is elongate to allow movement therein of its respective insert along the first line and the other of the bores cooperates with its respective insert so that the insert within the other of the bores is not movable within the other of the bores along the first line.

22. The plate system according to claim 1 wherein the first fastener has a first axis and is movable in a direction along the first axis through the first bore and the first insert piece extends only partially around the first axis with the first fastener extended through the first bore and between a part of each of the first and second insert pieces.

23. The plate system according to claim 22 wherein the second insert piece extends only partially around the first axis with the first fastener extended in a direction along the first axis through the first bore between the parts of each of the first and second insert pieces.

24. The plate system according to claim 22 wherein the first and second insert pieces are movable relative to each other in a direction transverse to the first axis.

* * * * *